United States Patent [19]

Larrabee

[11] 3,993,063

[45] Nov. 23, 1976

[54] PROTECTIVE SHIELDING ASSEMBLY FOR USE IN LOADING A HYPODERMIC SYRINGE WITH RADIOACTIVE MATERIAL

[75] Inventor: Edward W. Larrabee, Bronxville, N.Y.

[73] Assignee: Union Carbide Corporation, New York, N.Y.

[22] Filed: June 16, 1975

[21] Appl. No.: 587,179

[52] U.S. Cl. ............................. 128/215; 128/272.3; 250/515
[51] Int. Cl.² ......................................... A61M 5/00
[58] Field of Search ........ 128/215, 216, 218, 272.3; 250/515, 432, 108

[56] References Cited
UNITED STATES PATENTS

| | | | |
|---|---|---|---|
| 3,336,924 | 8/1967 | Sarnoff | 128/272 |
| 3,397,694 | 8/1968 | Ogle | 128/272 |
| 3,596,659 | 8/1971 | Glasser | 128/215 |
| 3,820,541 | 6/1974 | Langan | 128/215 |
| 3,872,867 | 3/1975 | Killinger | 128/272 |

*Primary Examiner*—John D. Yasko
*Attorney, Agent, or Firm*—Israel Blum

[57] ABSTRACT

The disclosure of this application is directed to a protective shielding assembly suitable for use in the loading of a hypodermic syringe with radioactive material. The protective shielding device receives and securely holds, at one end, a vial which contains the material to be loaded and at its opposite end a hypodermic syringe with the needle of the syringe approximately centered with respect to the septum of the vial. Penetration of the septum of the vial is effected by moving the slidable members of the protective shielding assembly toward the vial which in turn moves the hypodermic syringe causing the needle of the hypodermic syringe to rupture the vial septum and enter the vial.

3 Claims, 4 Drawing Figures

PROTECTIVE SHIELDING ASSEMBLY FOR USE IN LOADING A HYPODERMIC SYRINGE WITH RADIOACTIVE MATERIAL

This invention relates to an assembly suitable for use in the loading of a hypodermic syringe, especially the loading of a hypodermic syringe with radioactive material or a solution thereof. More particularly, this invention relates to a protective shielding assembly, suitable for use in the loading of a hypodermic syringe with radioactive material, which can be readily engaged to and disengaged from a dose vial and a hypodermic syringe, provides an accurate alignment of the needle of the hypodermic syringe with the center of the vial septum to be penetrated, controls the degree of penetration of the vial by the needle of the hypodermic syringe and protects the person who is loading the syringe from exposure to radiation emitted by the radioactive material.

Currently, radioactive material is widely used in the diagnosis and treatment of various diseases and body disorders. The radioactive material is generally injected into the body of a patient by means of a hypodermic syringe. Injection of a patient with radioactive material by means of a hypodermic syringe has been found to present serious health hazards to the person preparing and administering the injection. This is due to radioactivity emanating from the radioactive material which is to be injected.

As a result of the health hazards presented, it has been proposed to shield both the vial, containing the radioactive material and the hypodermic syringe which is to be loaded, with material, such as lead and lead glass, which is substantially impervious to the passage of radioactive emissions. As a rule, this has been accomplished with respect to the vial, by placing the vial in a snug-fitting sheath of lead which extends to the shoulders of the vial. The hypodermic syringe is shielded, generally, by a lead-glass shield which surrounds the barrel of the hypodermic syringe.

The shielding of the dose vial and hypodermic syringe, as described, although affording some protection to the person loading and discharging the loaded hypodermic syringe does not provide adequate protection during the loading operation. Conequently, during the loading operation, the technician or operator is subjected to an undesirable amount of radiation.

The present invention is a shielding assembly which affords greater protection to the person loading a hypodermic syringe with radioactive material and in addition provides advantages previously described.

Further advantages of the present invention are readily apparent from the following description and from the accompanying drawings wherein.

Figure 1:
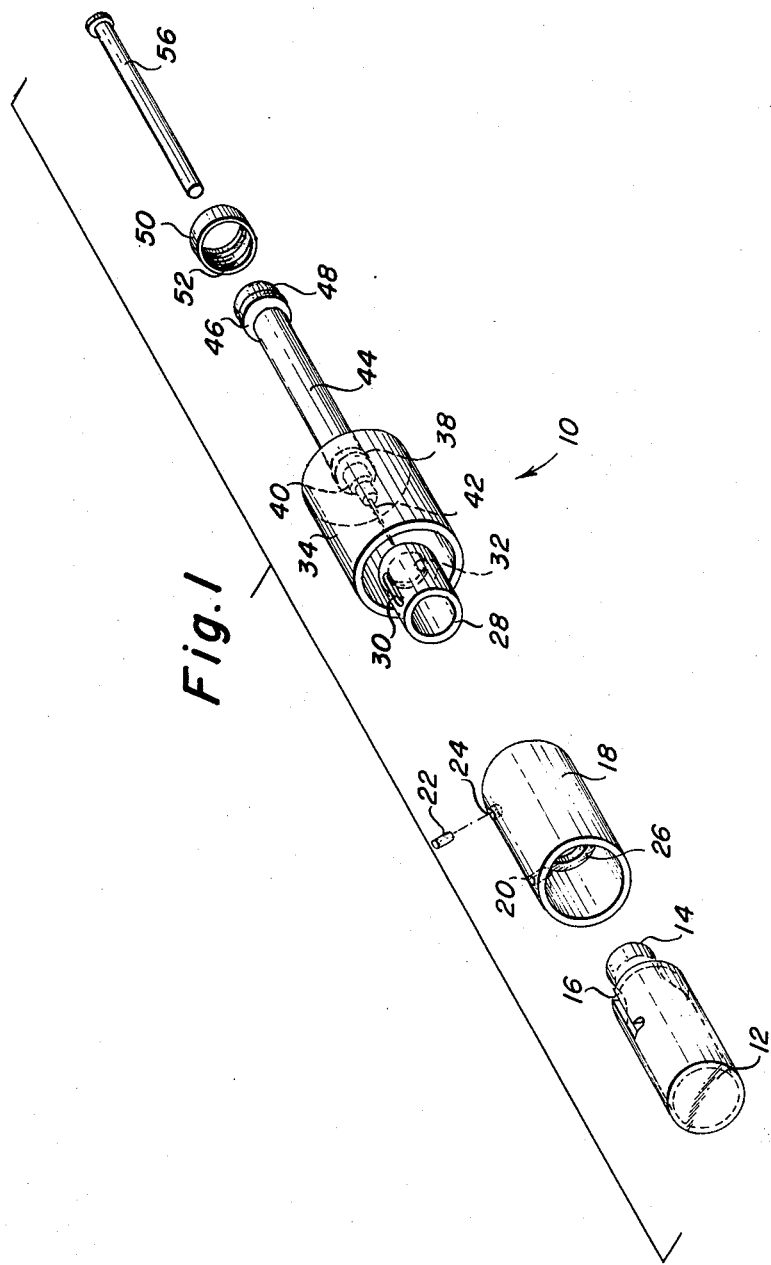
FIG. 1 is an exploded perspective view of the shielding assembly of this invention in conjunction with a dose vial and a hypodermic syringe.
Figure 2:
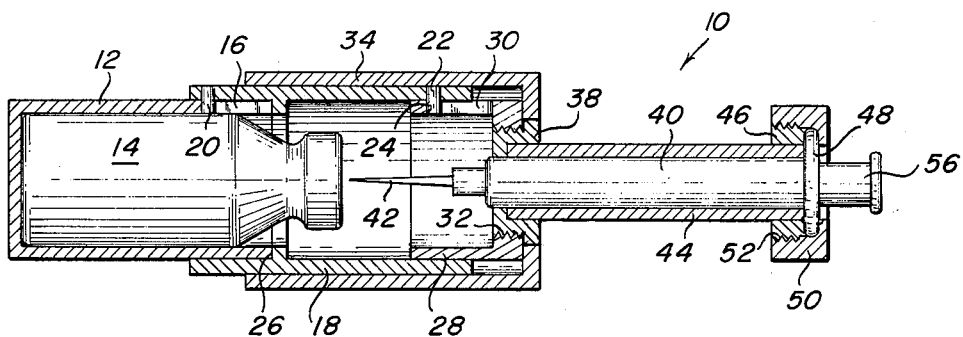
FIG. 2 is a longitudinal section of the shielding assembly connected to the dose vial and hypodermic syringe, prior to penetration of the dose vial.
Figure 3:
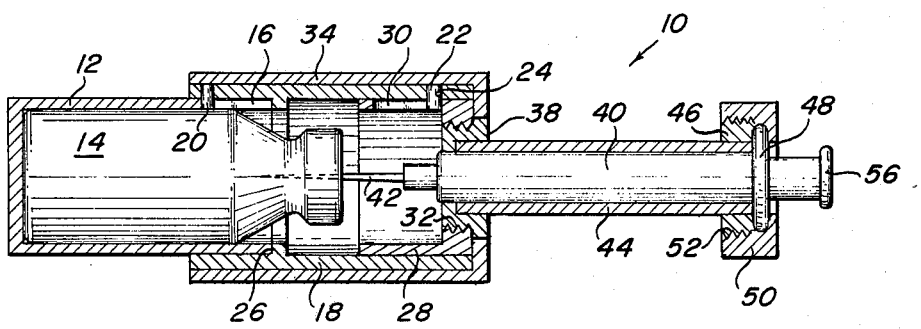
FIG. 3 is a longitudinal section, similar to FIG. 2, showing the shielding assembly in a vial puncturing position
Figure 4:
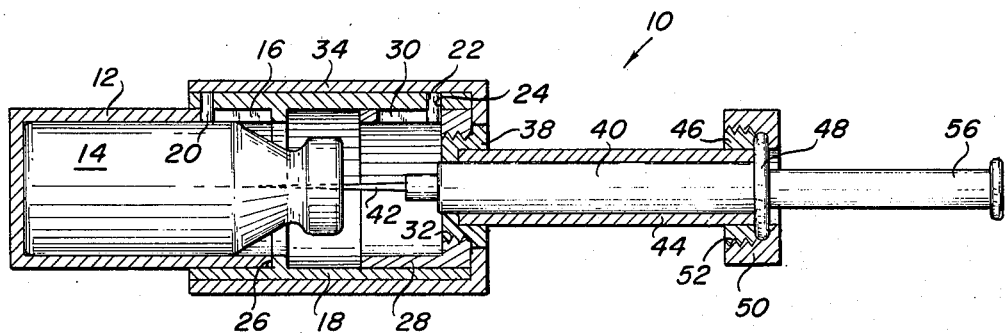
FIG. 4 is a longitudinal section, similar to FIGS. 2 and 3, showing the plunger of the hypodermic syringe withdrawn, loading the barrel of the syringe.

Referring now to FIG. 1 of the accompanying drawings, the protective shielding assembly of this invention designated in general by numeral 10 comprises three main functional members, those being an inner, slidable needle alignment sleeve 28, an intermediate sleeve 18 and an outer, cap-like, protective shield 34 which slides in conjunction with inner sleeve 28, relative to intermediate sleeve 18, the three members, when assembled, being in contact as shown in FIGS. 2, 3 and 4.

The pretective shielding assembly of this invention is adapted for the loading of a hypodermic syringe, the parts of which are identified in the drawings as: needle 42, syringe barrel 40, and syringe plunger 56; with the contents from a standard vial designated by numeral 14.

In the embodiment shown in the drawings, inner slidable needle alignment sleeve 28 has a longitudinal slot 30 and a rear threaded section 32 for receiving complementary threaded section 38 which is adhesively attached to syringe shield 44, as will be subsequently discussed. Needle alignment sleeve 28 fits snugly within but in slidable relationship to intermediate sleeve 18 with longitudinal slot 30 of sleeve 28 aligned with hole 24 of intermediate sleeve 18. Once sleeve 28 is placed within intermediate sleeve 18 and aligned, as described, pin 22 is pressed flush into hole 24 and extends into longitudinal slot 30 of needle alignment sleeve 28. Pressed pin 22 rides in longitudinal slot 30 and limits the degree of forward and rearward movement of needle alignment sleeve 28 relative to intermediate sleeve 18, as shown in FIGS. 2, 3 and 4.

The actual length of needle alignment sleeve 28 and of longitudinal slot 30 therein are such as to allow for complete penetration of vial 14, to a desired depth, by needle 42 of the hypodermic syringe as shown in FIGS. 3 and 4 of the drawings.

With needle alignment sleeve 28 and intermediate sleeve 18 connected, as described, outer cap-like sleeve or protective shield 34 is slidably mounted over intermediate sleeve 18 and connected to the back side of threaded section 32 of needle alignment sleeve 28 by any convenient means, as for example, screws (not shown). The protective shield 34 is of a length to overlap, at all times, vial shield 12.

The protective shielding assembly, with its three members assembled and coaxially mounted is ready to receive and securely hold syringe sheath 44, through which the hypodermic syringe is to be slidably inserted. In the embodiment shown in the accompanying drawings, this is accomplished by providing syringe sheath 44 with a threaded member 38 which threads into threaded member 32 of needle alignment sleeve 28. Consequently, syringe sheath 44 is simply screw threaded into the protective shielding assembly. The size and configuration of threaded sections 38 and 32 are such as to accurately align needle 42 of the hypodermic syringe with the center of the septum of vial 14, as shown in FIGS. 2, 3 and 4.

Threaded member or fitting 38 is conveniently attached to syringe shield 44 by use of a suitable bonding agent such as an epoxy resin. A detailed description of suitable epoxy resin compositions appears in U.S. Pat. No. 3,788,321 to Thomas D. Reitler.

Syringe sheath 44 is also provided, at its end opposite threaded member 38, with threaded member or fitting 46. Threaded member 46 in conjunction with cap-nut 50, having threads 52, locks flange 48 of the hypodermic syringe within syringe sheath 44, once the hypodermic syringe is inserted into syringe sheath 44 to a position shown in FIG. 2.

The entire assembly is then connected to vial 14.

This is conveniently accomplished, as shown in the drawings, by providing intermediate sleeve 18 with an internally extending pin 20, which fits into bayonet slot 16 of vial shield 12 which surrounds vial 14. Intermediate sleeve 18 is locked to vial shield 12 by turning to dispose pin 20 in the hooked end of bayonet slot 16. With pin 20 disposed in the hooked end of bayonet slot 16, locking intermediate sleeve 18 to vial shield 14, internal, annular shoulder 26 of intermediate sleeve 18 rests against the front face of vial shield 12 forming a close fit therewith.

FIG. 2 of the accompanying drawings shows the protective shielding assembly, providing complete shielding protection, connected to vial 14 with the hypodermic syringe in position ready for use.

On applying force to the protective shield assembly in the direction of vial 14, the hypodermic syringe, and needle alignment sleeve 28 and sleeve 34 of the protective shielding assembly move toward vial 14 resulting in syringe needle 42 puncturing the septum of vial 14 and penetrating vial 14 as shown in FIG. 3. The depth of penetration of syringe needle 42 in vial 14 is controlled by the length of longitudual slot 30 in needle alignment sleeve 28. Penetration of syringe needle 42 into vial 14 is stopped when pressed pin 22 abuts the inner wall of needle alignment sleeve 28 as shown in FIG. 3.

Loading of the hypodermic syringe is carried out by withdrawing plunger 56 of the hypodermic syringe as shown in FIG. 4.

The loaded hypodermic needle is then returned to the position shown in FIG. 2 by simply retracting the hypodermic needle from vial 14.

Removal of the loaded hypodermic syringe from protective shield assembly is effected by unscrewing syringe sheath 44 from the protective shielding assembly. The loaded hypodermic syringe can then be used in an injection operation.

After the injection operation, the hypodermic syringe can be removed from the syringe sheath by unscrewing cap-nut 50 from threaded member 46.

The protective shielding assembly of this invention can be used with standard glass vials and hypodermic needles. The glass vials generally have rubber septums held in place by a crimped aluminum cap. The shield which surrounds the glass vial can be of any material which is substantially impervious to the passage of radioactive emissions although lead is preferred.

Although the present invention has been exemplified in reference to a bayonet locking mechanism between the vial shield 12 and intermediate sleeve 18, it is to be understood that a friction fit can be used to secure vial shield 12 to intermediate sleeve 18.

Intermediate sleeve 18 and needle alignment sleeve 28 can be of any suitable material such as aluminum or other metals or plastic. Outer sleeve or protective shield 34 is also usually made of lead.

The shield 44 surrounding the barrel 40 of the hypodermic syringe is generally made of lead-glass to allow observation of the amount of material in barrel of the hypodermic syringe. Threaded members 38 and 46 which are adhesively attached to shield 44 are usually metal but can be plastic, if so desired, as can be the locking assembly for flange 48.

Also, if desired, a protective cap can be mounted over locking nut 50 to provide a shield around the plunger area when the plunger is withdrawn as shown in FIG. 4.

It is to be understood that whenever lead is indicated to be used lead alloys can be substituted.

As an alternative to the protective shielding assembly described and disclosed in the drawings, outer cap-like shield 34 can be eliminated by making intermediate sleeve 18 and inner sleeve 28 of a material which is substantially impervious to the passage of radioactive emissions, particularly gamma rays; and by extending inner sleeve 28 towards the vial and moving slot 30 and pin 22 correspondingly the sleeve 28 will cover slot 30 at all times allowing outer shield 34 to be removed without leaving an uninterrupted path for radiation.

What is claimed is:

1. A protective shielding assembly, suitable for use in the loading of a hypodermic syringe, adapted at one end to be connected to a protective shield surrounding a vial and at its opposite end adapted to be connected to a protective shield, surrounding the barrel of a hypodermic syringe at the needle end thereof and fixedly holding the hypodermic syringe comprising an inner sleeve, an intermediate sleeve connectable to the protective shield surrounding the vial, and an outer protective sleeve connected to said inner sleeve, said outer sleeve and said inner sleeve being in contact with and slidable with respect to said intermediate sleeve, said slidable members capable of moving the protective shield fixedly holding the hypodermic syringe toward the vial causing penetration thereof by the needle of the hypodermic syringe.

2. A protective shielding assembly, suitable for use in the loading of a hypodermic syringe, adapted at one end to be connected to a protective shield surrounding a vial and at its opposite end adapted to be connected to a protective shield, surrounding the barrel of a hypodermic syringe at the needle end thereof and fixedly holding the hypodermic syringe comprising, as concentrically mounted members, an inner sleeve, an intermediate sleeve connectable to the protective shield surrounding the vial and an outer protective cap-like sleeve overlapping the shield surrounding the vial and connected to said inner sleeve, said outer-cap like sleeve and said inner sleeve in contact with and slidably movable with respect to said intermediate sleeve, said slidable members on being moved toward the vial effecting movement of the protective shield surrounding the barrel of the hypodermic syringe toward the vial causing penetration thereof by the needle of the hypodermic syringe.

3. A protective shielding assembly, suitable for use in the loading of a hypodermic syringe, adapted at one end to be connected to a protective shield surrounding a vial and at its opposite end adapted to be connected to a protective shield, surrounding the barrel of a hypodermic syringe at the needle end thereof and fixedly holding the hypodermic syringe comprising an inner sleeve having a longitudinal slot therein and mounted within an intermediate sleeve, said intermediate sleeve having a pin extending through the wall thereof and riding in the slot of said inner pin, said pin limiting the degree of slidable movement of said inner sleeve, an outer cap-like protective sleeve slidable mounted on said intermediate sleeve and connected to said inner sleeve, said slidable members capable of moving the protective shield fixedly holding the hypodermic syringe toward the vial causing penetration thereof by the needle of the hypodermic syringe.

* * * * *